United States Patent [19]

Kaltenbach, III et al.

[11] Patent Number: 5,376,664

[45] Date of Patent: Dec. 27, 1994

[54] UNSYMMETRICAL MONO-3-NITRO BIS-NAPHTHALIMIDES AS ANTICANCER AGENTS

[75] Inventors: Robert F. Kaltenbach, III, New Castle; Jung-Hui Sun, Hockessin; Robert J. Cherney, Newark; Steven P. Seitz, Swarthmore, all of Del.

[73] Assignee: The Du Pont Merck Pharmaceutical Company, Wilmington, Del.

[21] Appl. No.: 16,553

[22] Filed: Feb. 11, 1993

Related U.S. Application Data

[63] Continuation-in-part of Ser. No. 919,227, Jul. 27, 1992, abandoned.

[51] Int. Cl.$^5$ .................... A61K 31/445; C07D 221/10
[52] U.S. Cl. ........................................ 514/296; 546/99
[58] Field of Search ......................... 546/99; 514/296

[56] References Cited

U.S. PATENT DOCUMENTS

| | | |
|---|---|---|
| 4,841,052 | 6/1989 | Harnisch et al. . |
| 4,874,863 | 10/1989 | Brana et al. . |
| 4,919,848 | 4/1990 | Harnisch . |
| 5,206,249 | 4/1993 | Sun ........................................ 514/296 |

FOREIGN PATENT DOCUMENTS

WO9217453 10/1992 WIPO .

*Primary Examiner*—Johann Richter
*Assistant Examiner*—Michael B. Hydorn
*Attorney, Agent, or Firm*—Blair Q. Ferguson

[57] ABSTRACT

This invention relates to unsymmetrical mono-3-nitro bis-naphthalimides of formula

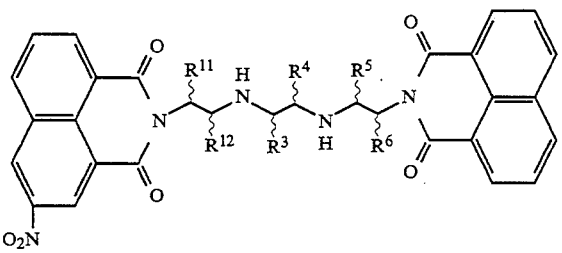

including (R,R)-2-{2-[2-((2-(1,3-dioxo-1H-benz-[de]isoquinolin-2-(3H)-yl)-propylamino))ethylamino]-1-methylethyl}-5-nitro-1H-benz[de]isoquinolin-1,3-(2H)-dione, processes for their preparation, pharmaceutical compositions containing them, and methods of using them to treat cancer, particularly solid tumor carcinomas, in mammals.

8 Claims, No Drawings

UNSYMMETRICAL MONO-3-NITRO BIS-NAPHTHALIMIDES AS ANTICANCER AGENTS

CROSS REFERENCE TO EARLIER FILED APPLICATION

This application is a continuation-in-part application of U.S. patent application Ser. No. 07/919,227, filed Jul. 27, 1992, now abandoned.

FIELD OF THE INVENTION

This invention relates to unsymmetrical mono-3-nitro bis-naphthalimides of formula

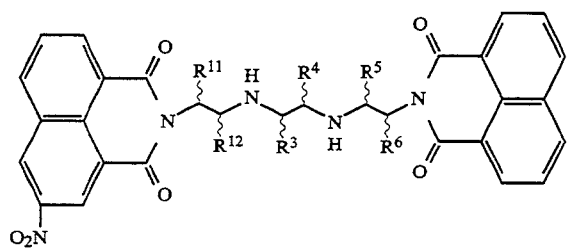

including (R,R)-2-{2-[2-((2-(1,3-dioxo-1H-benz[de]isoquinolin-2-(3H)-yl)-propylamino))ethylamino]-1-methylethyl}-5-nitro-1H-benz[de]isoquinolin-1,3-(2H)-dione, processes for their preparation, pharmaceutical compositions containing them, and methods of using them to treat cancer, particularly solid tumor carcinomas, in mammals.

BACKGROUND OF THE INVENTION

Harnisch et al., U.S. Pat. No. 4,841,052 issued Jun. 20, 1989 describe naphthalic acid imides useful as charge-regulating substances in electrophotographic toners.

Brana et al., U.S. Pat. No. 4,874,863 issued Oct. 17, 1989 discloses anticancer compounds of the formula:

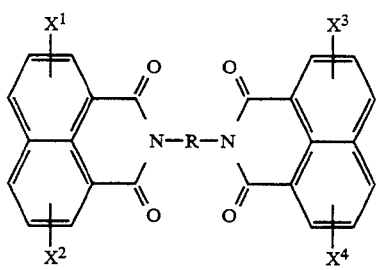

wherein $X^1$, $X^2$, $X^3$ and $X^4$ are identical or different and are each H, $NO_2$, $NH_2$, $C_1$-$C_6$-alkylamino, di-$C_1$-$C_6$-alkylamino, OH, $C_1$-$C_6$-alkoxy, halogen, trihalomethyl, $C_1$-$C_6$ alkyl, formyl, $C_1$-$C_6$-alkylcarbonyl, ureyl, $C_1$-$C_6$-alkylureyl and R is a straight chain or branched $C_4$-$C_{10}$-alkylene which is interrupted at one or two points in the chain by a secondary or tertiary amino group, where 2 nitrogen atoms may additionally be bonded to one another by an alkylene group, or a salt with a physiologically tolerated acid.

Brana et al., U.S. Pat. No. 4,874,863 does not specifically disclose the compounds of the present invention.

The compounds of the present invention have unexpectedly increased water solubility compared to certain compounds specifically disclosed in U.S. Pat. No. 4,874,863. This is an important advantage, since the less soluble compounds present serious problems when trying to formulate such compounds into a dosage form suitable for human use.

In addition the compounds of the present invention exhibit unexpected superior antitumor activity relative to the compounds specifically disclosed by Brana et al.

DETAILED DESCRIPTION OF THE INVENTION

There is provided by this invention bis-naphthalimide compounds having the formula (i):

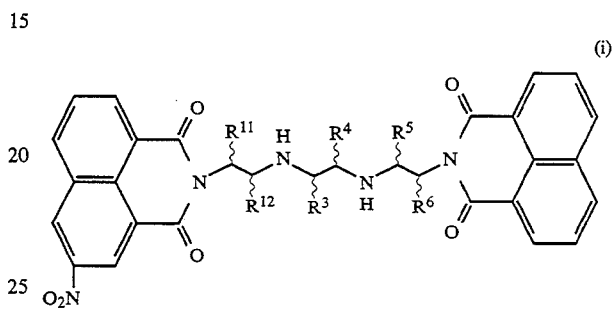

or enantiomeric or diastereomeric forms thereof, or mixtures of enantiomeric or diastereomeric forms thereof, or pharmaceutically acceptable salts thereof, wherein:

$R^{11}$, $R^{12}$, $R^3$, $R^4$, $R^5$, and $R^6$, independently, are H or $CH_3$.

Preferred compounds of the present invention include those compounds of formula (i) wherein:

$R^{11}$ and $R^6$ are $CH_3$; and $R^{12}$, $R^3$, $R^4$, and $R^5$ are H.

The specifically preferred compounds of the present invention are the following, and pharmaceutically acceptable salts thereof:

(R,R)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione;

(S,S)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione;

(racemate+meso)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione; and (meso)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione.

Also provided by this invention are processes for the preparation of the compounds of formula (i), pharmaceutical compositions containing the compounds of formula (i), and methods of using these compounds for the treatment of cancer, particularly solid tumor carcinomas, in a mammal.

The present invention includes methods of preparing a compound having the formula (i):

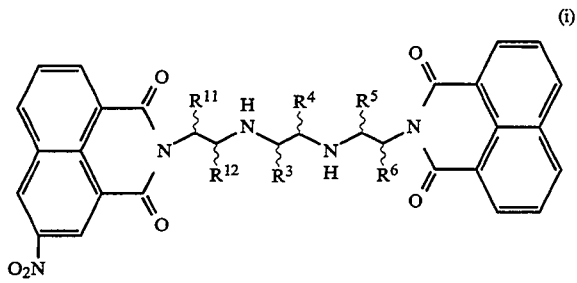

or enantiomeric or diastereomeric forms thereof, or mixtures of enantiomeric or diastereomeric forms thereof, and pharmaceutically acceptable salts thereof, wherein:

$R^{11}$, $R^{12}$, $R^3$, $R^4$, $R^5$, and $R^6$, independently, are H or $CH_3$;

said method comprising the steps of:
(1) reacting a polyamine of formula:

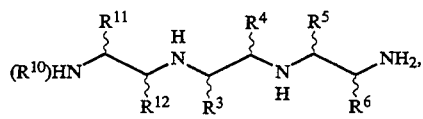

wherein $R^{10}$ is a subtituted arylsulfonyl protecting group;
with an anhydride of formula (ii)

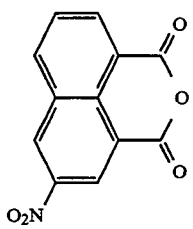

or
formula (iii)

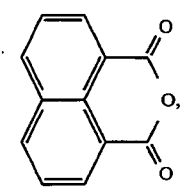

to obtain a naphthalimide of formula

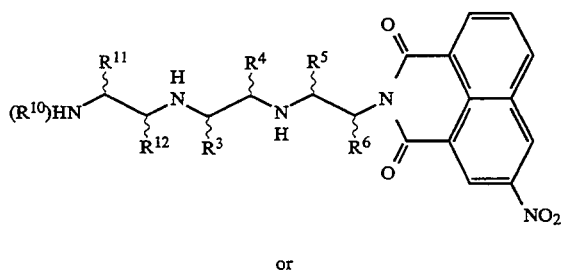

or

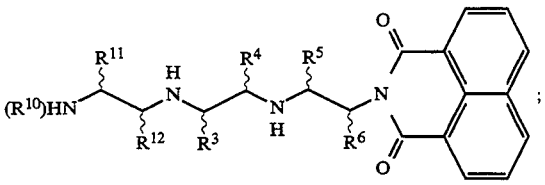

(2) removing the protecting group $R^{10}$ from the naphthalimide of step (1) to obtain a deprotected naphthalimide;

(3) reacting the deprotected naphthalimide of step (2) with an anhydride of formula (ii) or formula (iii), to obtain the compound of formula (i).

$R^{10}$ is a substituted arylsulfonyl protecting group, for example arylsulfonyl groups wherein the aryl group is substituted with 0-5 groups selected independently from: phenyl, benzyl, phenethyl, phenoxy, benzyloxy, halogen, hydroxy, nitro, cyano, $C_1$-$C_5$ alkyl, $C_3$-$C_6$ cycloalkyl, $C_3$-$C_6$ cycloalkylmethyl, $C_7$-$C_{10}$ arylalkyl, $C_1$-$C_4$ alkoxy, formyl, $C_3$-$C_6$ cycloalkoxy, $C_2$-$C_6$ alkoxyalkyl, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino.

A preferred $R^{10}$ is the mesitylenesulfonyl group.

Further examples of substituted arylsulfonyl protecting groups are described, for example, in Greene and Wutz, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference.

As used herein, "aryl" or "aromatic residue" is intended to mean phenyl or naphthyl. As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

The compounds of the present invention, although encompassed within the broad scope of U.S. Pat. No. 4,874,863, are not specifically claimed or exemplified therein. Brana et al. do not describe the synthesis of any unsymmetrical bis-naphthalimides. Moreover, the compounds of the present invention were discovered to have significantly increased antitumor activity relative to the compounds specifically disclosed in Brana et al., U.S. Pat. No. 4,874,863. Whereas the compounds of the present invention exhibit very efficacious in vivo activity against solid tumors, the structurally similar compounds specifically disclosed by Brana et al. were found to be inactive.

In addition, the bis-naphthalimides of the present invention were found to have increased water solubility relative to certain compounds specifically disclosed by Brana et al.

Compounds of the present invention can be synthesized using the methods described below, together with synthetic methods known in the art of synthetic organic chemistry. The references cited below are all incorporated herein by reference.

Compounds of this invention can be synthesized by reacting approximately equimolar amounts of the corresponding anhydrides of formula (ii) and (iii) and polyamine of formula (iv) in a suitable solvent, said solvent being substantially nonreactive with the starting materials and products (i.e., any of the compounds of formula (i), (ii), (iii), or (iv)), at a temperature ranging from ambient to the solvent's boiling temperature (Scheme A). Suitable solvents include but are not limited to, for example, ethanol, DMSO, dimethylformamide, or tetrahydrofuran.

The resulting free base of (i) can be acidified with the appropriate mineral or organic acid in ethanol or dichloromethane, for example, to produce a pharmaceutically acceptable salt. Generally, pharmaceutically acceptable salts of the compounds of the invention can be prepared by reacting the free base form of these compounds with a stoichiometric amount of the appropriate acid in an organic solvent or in water, or in a mixture of the two; generally, nonaqueous media like ether, dichloromethane, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference. The free base of (i) may require purification by techniques such as column chromatography, recrystallation, or distillation for example, as well as other techniques well known to those skilled in the art of organic synthesis before its salt can be prepared as described above.

(D)-alanine with 1,1'-carbonyldiimidazole (CDI) followed by reaction with ethylenediamine under standard conditions to give the diamide II. Acid hydrolysis of the BOC (N-tert-butoxycarbonyl) protecting group, followed by reduction with diborane in refluxing tetrahydrofuran and acidic workup afforded III, which can be neutralized to give the pure free base IV. By treating equimolar amounts of the corresponding anhydrides ii and iii with IV in tetrahydrofuran at reflux temperature, the unsymmetrical freebase Ib is obtained after purification on silica gel. The resulting free base is acidified with an appropriate mineral or organic acid in dichloromethane, for example methanesulfonic acid to produce the pharmaceutically acceptable salt Ia.

Procedures for the synthesis of the diastereomeric or enantiomeric forms of the polyamine linker IV or mixtures of enantiomeric or diastereomeric forms thereof are fully described in commonly assigned, copending patent application U.S. Ser. No. 07/805,044, filed Dec. 11, 1991.

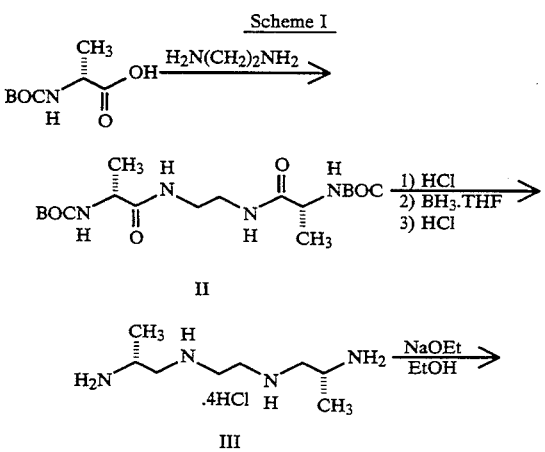

Scheme I

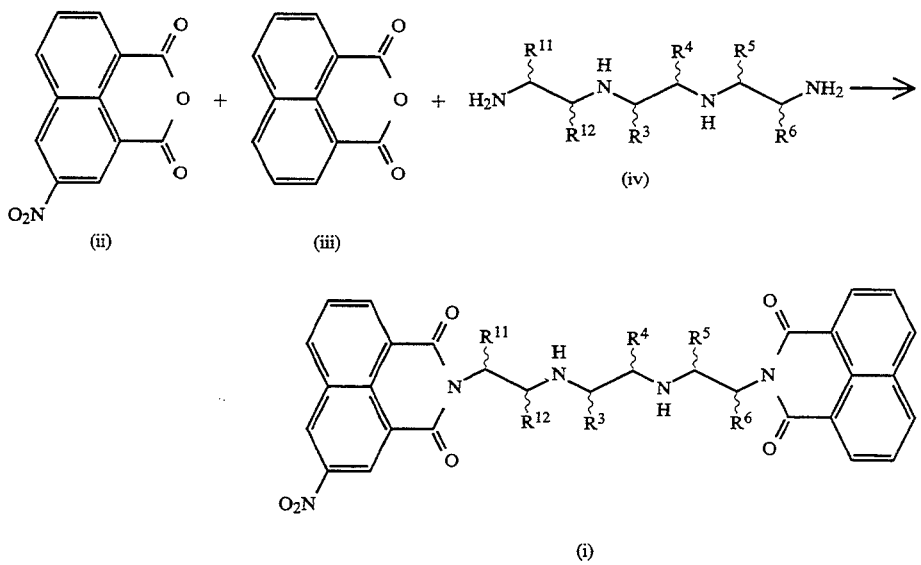

Scheme A

The anhydrides (ii) and (iii) are commercially available. Polyamines of formula (iv) can be prepared according to the methods described below.

For example the synthesis of compounds of formula I where $R^{11}=R^6=CH_3$, $R^{12}=R^3=R^4=R^5=H$, (see Scheme I) can be accomplished by the reaction of BOC- Scheme I
-continued

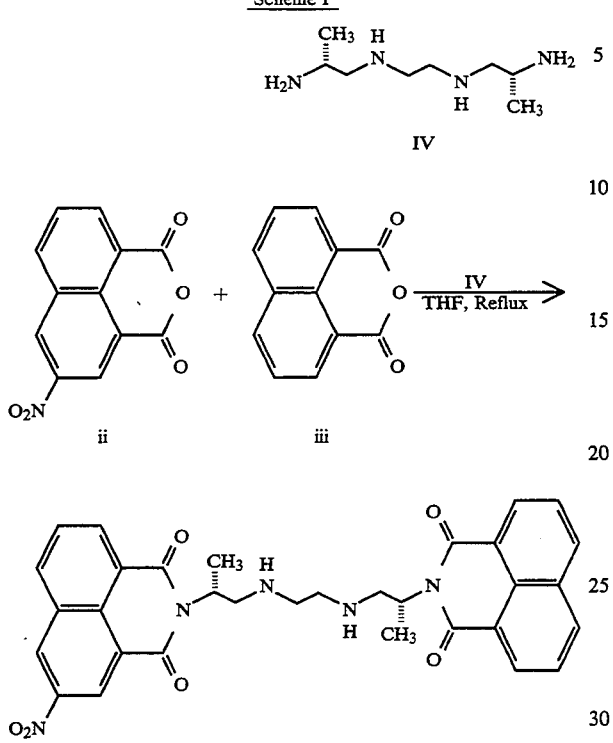

Ia Bis-Methanesulfonate
Ib Freebase

The compound of formula I can also be synthesized by an alternative process via a stepwise condensation of anhydrides ii and iii onto a differentially protected linker (see scheme II). This procedure commences with the CDI coupling of N-mesitylenesulfonyl-D-alanine (V) (Ger. Patent DE 2544859, 1976) and N-tert-butoxycarbonyl- 1,2-ethanediamine (Krapcho, Syn. Comm. 1990, 20(16), 2559) to yield the amide VI. The BOC protecting group of amide VI was then removed under acidic conditions, and the resulting salt was treated with sodium carbonate to afford the free base VII. This material was then subjected to a CDI coupling with N-BOC-D-alanine, acid removal of the BOC group, and subsequent treatment with sodium carbonate to yield the diamide IX. The amide bonds of IX were reduced with BH$_3$.THF to provide the key differentially protected linker X which was then condensed with the anhydride ii (or iii) to yield the mono-naphthalimide XI (or XII). At this point, the mesitylenesulfonyl group was removed with 30% HBr/acetic acid to afford the crystalline salt XIII (or XIV). Treatment with sodium carbonate gave the freebase, which was condensed with the appropriate anhydride iii (or ii) to give the freebase Ib. This free base can be acidified with the appropriate mineral or organic acid as described above to produce a pharmaceutically acceptable salt.

Scheme II

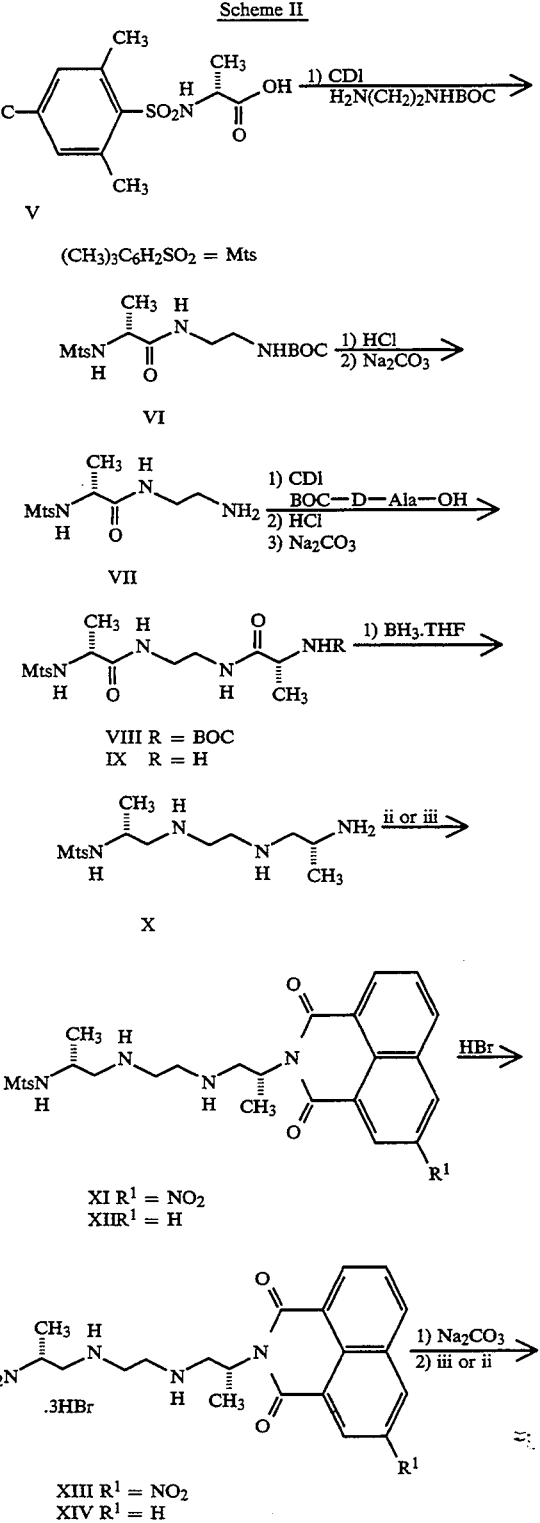

$(CH_3)_3C_6H_2SO_2$ = Mts

VIII R = BOC
IX R = H

XI R$^1$ = NO$_2$
XII R$^1$ = H

XIII R$^1$ = NO$_2$
XIV R$^1$ = H

Bis-naphthalimides of the formula XVI where R$^{11}$=R$^3$=R$^4$=R$^6$=H, R$^{12}$=R$^5$=CH$_3$ can be made as shown in Scheme III. By reacting equimolar amounts of the corresponding anhydrides of formula (ii) and (iii) with polyamines XV (a–d) in an inert solvent such as ethanol or dimethylformamide or tetrahydrofuran, for example, at a temperature ranging from ambient to the solvent's boiling temperature. The resulting free base of XV can be acidified with the appropriate mineral or organic acid to produce a pharmaceutically acceptable salt. Detailed procedures for the synthesis of the polyamine linkers XV (a–d) are described in commonly assigned, copending patent application U.S. Ser. No. 07/805,044, filed Dec. 11, 1991.

Scheme III

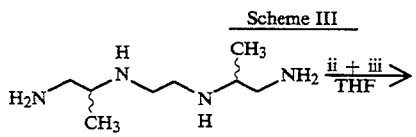

XVa, (S,S)
XVb, (R,R)
XVc, (racemate+meso)
XVd, (meso)

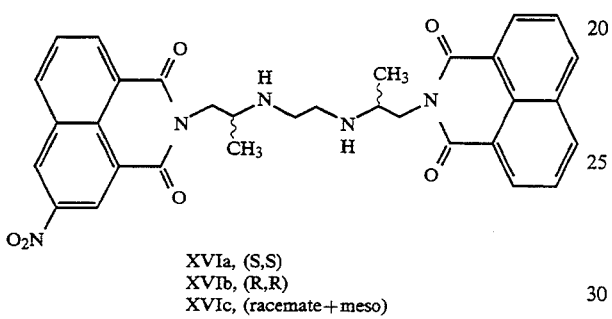

XVIa, (S,S)
XVIb, (R,R)
XVIc, (racemate+meso)
XVId, (meso)

Bis-naphthalimides of the formula XXV where $R^{12}=R^5=H$, $R^{11}=R^6=CH_3$, and $R^3$ or $R^4=CH_3$ can be prepared as shown in Scheme IV. As before, N-mesitylenesulfonyl-alanine V can be homologated under standard conditions with ammonia followed by reduction with $BH_3.THF$ to provide the amine XVII. Coupling to BOC-alanine with CDI followed by deprotection of the BOC protecting group, gives the amide XVIII. The linker is completed by another BOC-alanine coupling/BOC deprotection sequence to provide the diamide XIX. This material can then be reduced under the standard borane conditions to give the triamine XX. The first naphthalimide can be condensed onto the primary amine with ii or iii yielding the mono-naphthalimide XXI or XXII. Deprotection of the mesitylenesulfonyl protecting group with HBr/acetic acid can give the primary amine XXIII or XXIV. The synthesis can be completed by a second condensation with iii or ii to yield the desired unsymmetrical bis-naphthalimide XXV or XXVI.

Scheme IV

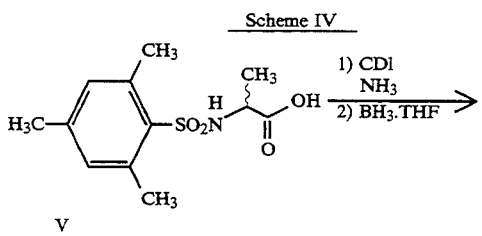

$(CH_3)_3C_6H_2SO_2$ = Mts

-continued
Scheme IV

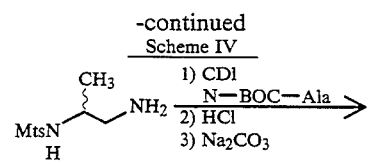

XVII

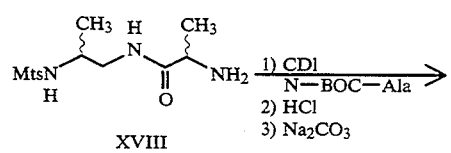

XVIII

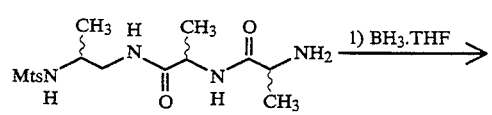

XIX

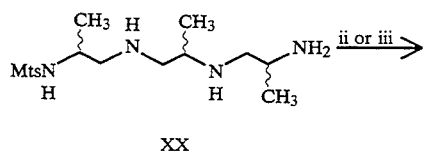

XX

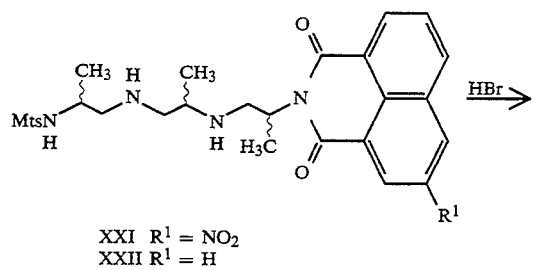

XXI $R^1 = NO_2$
XXII $R^1 = H$

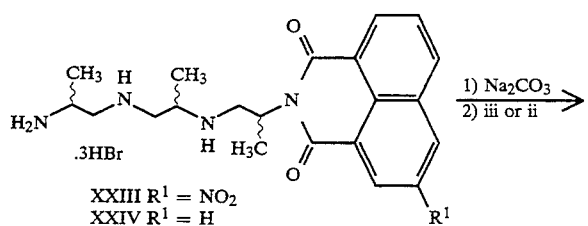

XXIII $R^1 = NO_2$
XXIV $R^1 = H$

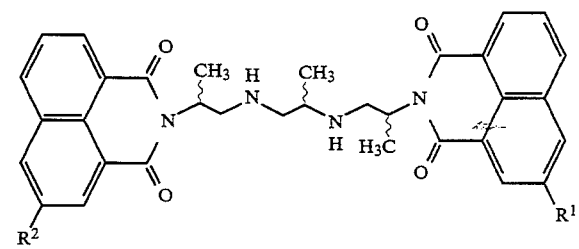

XXV $R^1 = NO_2$; $R^2 = H$
XXVI $R^1 = H$; $R^2 = NO_2$

Bis-naphthalimides of the formula XXXIV where $R^{12}=R^6=H$, $R^{11}=R^5=CH_3$ and $R^3$ or $R^4=CH_3$ can be obtained starting from N-mesitylenesulfonyl-alanine (V) (Scheme V). Standard CDI coupling of BOC-alanine and V followed by deprotection of the BOC protecting group gives the amide XXVII. Another CDI coupling with alaninamide gives the triamide XXVIII.

Borane reduction gives the differentially protected linker XXIX, which can be carried through the naphthalic anhydride condensation-HBr/acetic acid deprotection-naphthalic anhydride condensation sequence to provide the desired unsymmetrical bis-naphthalimide XXXIV or XXXV.

sulfonyl amine XXXVII under standard conditions. Lactic acid XXXVIII can be converted to the t-butyl ester triflate XXXIX and coupled with XXXVII, using chemistry described by Webb et. al., (*J. Org. Chem.*, p.4706 (1991)) to provide the amine XXXX. BOC deprotection, followed by CDI coupling with alanine methyl ester, and amidation with ammonia can provide the diamide XXXXII. Reduction of the diamide with borane provides the differentially protected polyamine linker XXXXIII. This material can then be taken through the naphthalic anhydride condensation-HBr/acetic acid deprotection-naphthalic anhydride condensation sequence to provide the desired unsymmetrical bis-naphthalimides XXXXVI or XXXXVII.

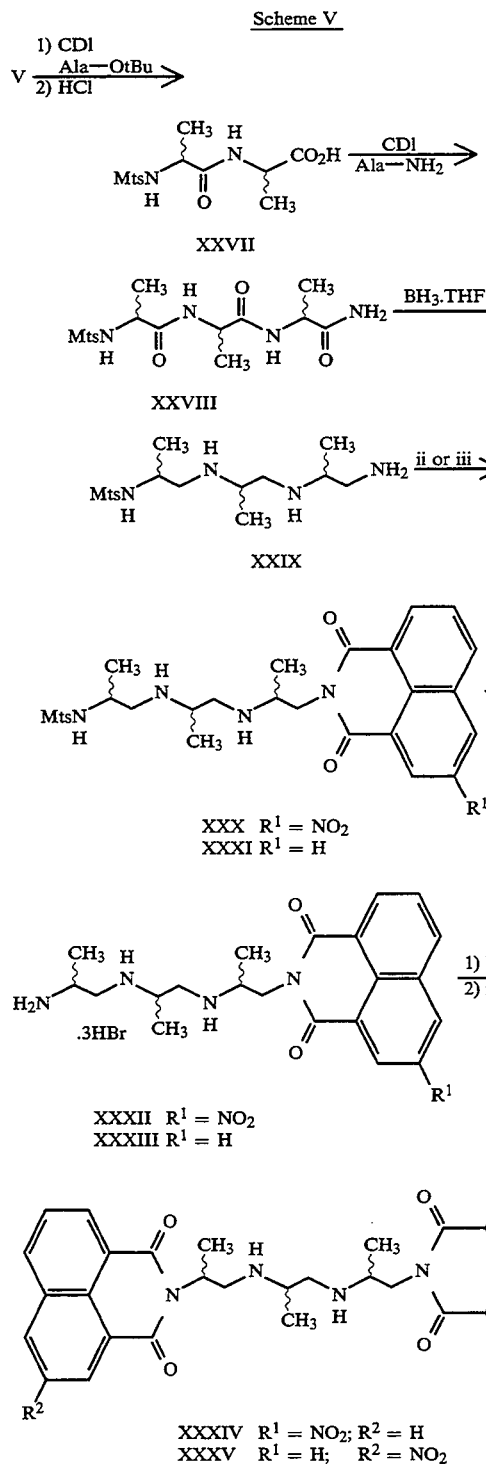

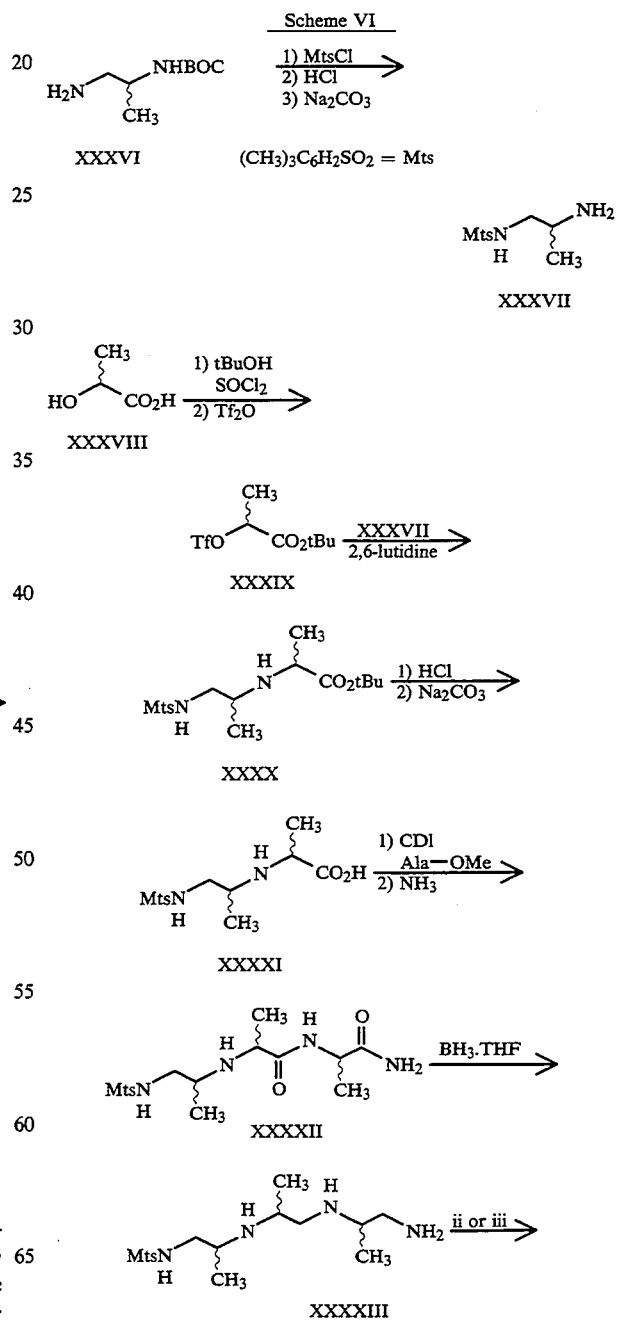

Bis-naphthalimides of the formula XXXXVI or XXXXVII where $R^{11}=R^6=H$, $R^{12}=R^5=CH_3$ and $R^3$ or $R^4=CH_3$ can be made as shown in Scheme VI. The BOC protected diamine XXXVI (PCT patent application WO 8504403 A1) is converted into the mesitylene- -continued
Scheme VI

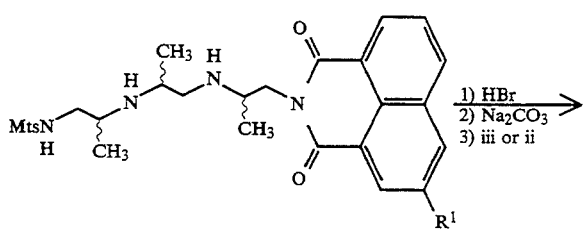

XXXXIV R¹ = NO₂
XXXXV R¹ = H

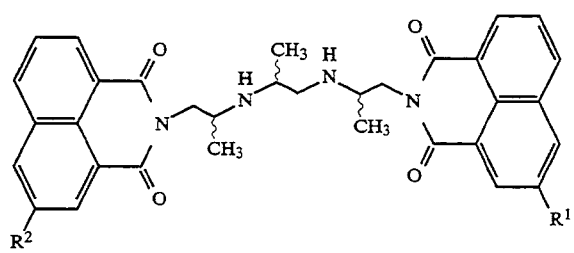

XXXXVI R¹ = NO₂; R² = H
XXXXVII R¹ = H; R² = NO₂

The compounds of this invention and their preparation are further understood by the following Example.

EXAMPLE 1

(R,R)-2-{2-[2-((2-(1,3-Dioxo-1H-benz[de]isoquinolin-2-(3H)-yl)-propylamino))ethylamino]-1-methylethyl}-5-nitro-1H-benz[de]isoquinolin-1,3-(2H)-dione bis-methanesulfonate (Ia)

Method A
Part A: Preparation of the di-BOC protected diamide (II).

To a stirred solution of 100 g (528 mmol) of t-BOC-D-alanine in 1500 mL of methylene chloride at 0° C. was added 89 g (549 mmol) of 1,1'-carbonyldiimidazole. After stirring 2.5 h, 17.6 mL (263 mmol) of ethylenediamine was added dropwise. After stirring 15 min., the suspension was warmed to room temperature and allowed to stir overnight. The mixture was then washed with saturated Na₂CO₃, water, and the organic layer was dried with anhydrous MgSO₄. The solvent was removed under reduced pressure to give 104 g (98%) of II as a white solid. ¹H NMR (300 MHz,CDCl₃) δ6.83 (broad s, 2H, NH), 5.18 (d, 2H, NH), 4.11 (m, 2H, CH), 3.48 (m, 2H, CH₂), 3.30 (m, 2H, CH₂), 1.44 (s, 18H, t-Bu), 1.35 (d, 6H, CH₃); MS (CI,CH₄) m/e 403 (M+1).

Part B: Reduction of II to give the polyamine salt (III).

To a stirred suspension of 51 g (127 mmol) of II in 100 mL of 1,4-dioxane was added 200 mL of a 4M solution of HCl in 1,4-dioxane. After stirring 4 h, the slurry was concentrated under reduced pressure. To the resulting solid 1450 mL of a 1M solution of BH₃.THF in THF was added and the suspension was refluxed overnight. The solution was then cooled to room temperature and 300 mL of methanol was added dropwise. The solution was refluxed 4 h, cooled to room temperature, concentrated under reduced pressure, and azeotroped with 500 mL of methanol. The resulting solid was then taken up in 500 mL of methanol and 35 mL of 37% aqueous HCl was added. The resulting suspension was heated on a steam bath 15 min., cooled to room temperature, and 800 mL of ether was added. The resulting white solid was then collected on a filter to give 38 g (93%) of III. ¹H NMR (300 MHz, D₂O) δ3.63 (m, 2H, CH), 3.38 (s, 4H,), 3.24 (m, 4H, CH₂), 1.28 (d, 6H, CH₃); MS (CI,CH₄) m/e 175 (M+1).

Part C Neutralization of III to yield the freebase (IV).

To a stirred slurry of 72.3 g (226 mmol) of III in 1450 mL of ethanol, was added 291 g of a 21% solution of sodium ethoxide in ethanol. After stirring 2 h, the mixture was filtered through celite, and the filtrate was concentrated under reduced pressure. Distillation of the crude amine under high vacuum gave 35.5 g (90%) of IV as a colorless oil. ¹H NMR (300 MHz, CDCl₃) δ2.95 (m, 2H, CH), 2.70 (m, 4H, CH₂), 2.55 (m, 2H, CH₂), 2.33 (m, 2H, CH₂), 1.37 (broad s, 6H, NH₂), 1.03 (d, 6H, CH₃); MS (CI,NH₃) m/e 175 (M+1).

Part D: Condensation of IV with the naphthalic anhydrides to give the bis-naphthalimide (I).

A solution of 500 mg (2.87 mmol) of IV in 10 mL of THF was added to a slurry of 697 mg (2.87 mmol) of 3-nitro-1,8-naphthalic anhydride and 568 mg (2.87 mmol) of 1,8-naphthalic anhydride in 20 mL of THF. The mixture was refluxed overnight and the dark suspension was cooled to room temperature. The solvent was removed under reduced pressure and the residue was chromatographed on silica gel. Elution with 5% methanol in methylene chloride gave 369 mg (23%) of the freebase Ib as a brown solid. ¹H NMR (300 MHz, CDCl₃) δ9.20 (s, 1H, aromatic), 9.06 (s, 1H, aromatic), 8.68 (d, 1H, aromatic), 8.50 (d, 2H, aromatic), 8.34 (d, 1H, aromatic), 8.16 (d, 2H, aromatic), 7.91 (t, 1H, aromatic), 7.72 (t, 2H, aromatic), 5.25 (m, 2H, CH), 3.43 (m, 2H, CH₂), 2.94 (m, 2H, CH₂), 2.77 (m, 4H, CH₂), 2.31 (s, NH), 1.47 (d, 3H, CH₃), 1.42 (d, 3H, CH₃); MS (CI,NH₃) m/e 580 (M+1).

The resulting freebase was converted to the bis-methanesulfonate by treatment with 78 μL (1.2 mmol) of methanesulfonic acid in 20 mL methylene chloride. After stirring overnight, the solid was collected by filtration to give 392 mg (18%) of Ia as a light tan powder. (mp 194°–199° C.).

The compound of formula I can also be synthesized by the alternate process described below.

Synthesis of I, Method B

Part A: Coupling of the protected diamine to give the amide (VI).

Mesitylenesulfonyl-D-alanine V (39.7 g, 140 mmol) was dissolved in 500 mL of methylene chloride and cooled to 0° C. prior to the addition of CDI (25.8 g, 160 mmol). After 2 h at 0° C., N-tert-butoxycarbonyl-1,2-ethanediamine (21.3 g, 130 mmol) in 10 mL of methylene chloride was added. The solution warmed to room temperature and stirred 12 h. The solution was then washed with saturated Na₂CO₃, H₂O, and 2% HCl. The methylene chloride was dried with anhydrous MgSO₄ and concentrated under reduced pressure to give 43.3 g (80%) of the amide VI as a white foam. ¹H-NMR (300 MHz, CDCl₃) δ6.96 (s, 2H, aromatic), 6.90 (broad s, 1H, NH), 5.65 (broad d, 1H, NH), 5.05 (broad s, 1H, NH), 3.67 (m, 1H, CH), 3.22 (m, 4H, CH₂), 2.63 (s, 6H, CH₃), 2.30 (s, 3H, CH₃), 1.43 (s, 9H, CH₃), 1.26 (d, 3H, CH₃); MS (CI,NH₃) m/e 414 (M+1).

Part B: Deprotection and neutralization to give the freebase (VII).

The amide VI (60.3 g, 146 mmol) was dissolved in 150 mL of dioxane and cooled to a ice bath prior to the addition of 210 mL (840 mmol) of a 4M solution of HCl in dioxane. The solution was warmed to room temperature and stirred for 4 h. The solvent was then removed under reduced pressure to give a solid, which was dissolved in 300 mL of saturated $Na_2CO_3$ and extracted with methylene chloride. The methylene chloride was dried with $Na_2CO_3$ and was concentrated under reduced pressure to give 37.6 g (89%) of the free base VII as a white foam. $^1$H-NMR (300 MHz, $CDCl_3$) $\delta$7.06 (m, 1H, 1 NH), 6.95 (s, 2H, aromatic), 3.68–3.57 (m, 1H), 3.26 (m, 2H, $CH_2$), 2.79 (t, 2H, $CH_2$), 2.62 (s, 6H, 2 $CH_3$), 2.30 (s, 3H, 1 $CH_3$), 1.22 (d, 3H, 1 $CH_3$); MS (CI,$NH_3$) m/e 314 (M+1).

Part C: Coupling to give the diamide (VIII).

The protected amino acid N-BOC-D-Ala (22.9 g, 120 mmol) was dissolved in 400 mL of methylene chloride and cooled to 0° C. prior to the addition of CDI (19.6 g, 120 mmol). The resulting mixture stirred 2 h at 0° C. before the amine VII (35.4 g, 110 mmol) suspended in 200 mL of methylene chloride was added dropwise. This mixture then warmed to room temperature and stirred 15 h. The solution was then washed with saturated $Na_2CO_3$, $H_2O$, and 2% HCl. The methylene chloride was dried with anhydrous $MgSO_4$ and concentrated under reduced pressure to give 41.2 g of the diamide VIII as a white foam. $^1$H-NMR (300 MHz, $CDCl_3$) $\delta$7.14 (broad s, 1H, NH), 6.96 (s, 2H, aromatic), 6.83 (broad s, 1H, NH), 5.92 (broad s, 1H, NH), 5.31 (broad s, 1H, NH), 4.10 (m, 1H, CH), 3.71 (m, 1H, CH), 3.4–3.2 (m, 2H, $CH_2$), 2.63 (s, 6H, $CH_3$), 2.30 (s, 3H, $CH_3$), 1.43 (s, 9H, $CH_3$), 1.22 (d, 3H, $CH_3$); MS (CI,$NH_3$) m/e 485 (M+1).

Part D: Deprotection and neutralization of the BOC protected amine to give IX.

The diamide VIII (41.2 g, 85 mmol) was dissolved in 10 mL of dioxane and cooled in an ice bath prior to the addition of 129 mL (510 mmol) of a 4M solution of HCl in dioxane. The solution was warmed to room temperature and stirred for 4 h. The solvent was then removed to give a solid, which was dissolved in 300 mL of saturated $Na_2CO_3$ and extracted with methylene chloride. The methylene chloride was dried with $Na_2CO_3$ and concentrated under reduced pressure to give 22.8 g (70%) of the free base IX as a white solid. $^1$H-NMR (300 MHz, $CDCl_3$) $\delta$7.68 (broad m, 1H, NH), 7.18 (broad m, 1H, NH), 6.96 (s, 2H, aromatic), 3.66 (m, 1H), 3.50–3.25 (m, 5H), 2.63 (s, 6H, $CH_3$), 2.3 (s, 3H, $CH_3$), 1.31 (d, 3H, $CH_3$), 1.23 (d, 3H, $CH_3$); MS (CI,$NH_3$); m/e 385 (M+1).

Part E: Reduction to give the polyamine (X).

The free amine IX (22.8 g, 59.4 mmol) was dissolved in 200 mL of THF prior to the addition of 1M $BH_3$.THF (594 mL, 594 mmol). This solution was refluxed for 15 h. After cooling, 200 mL of methanol was added, and the solution was refluxed an additional 4 h. The solution was then cooled and concentrated under reduced pressure. The resulting residue was dissolved in 150 mL of MeOH and cooled to 0° C. prior to the addition of 6 mL of concentrated HCl. This solution was concentrated under reduced pressure to a white solid, which was dissolved in saturated $Na_2CO_3$ and extracted with methylene chloride. The methylene chloride was dried with $Na_2CO_3$, and concentrated under reduced pressure to give 22.1 g (93%) of the free base X as a white foam. $^1$H-NMR (300 MHz, $CDCl_3$) $\delta$6.94 (s, 2H, aromatic), 3.63 (t, 1H), 3.23–3.17 (m, 1H), 2.99–2.93 (m, 1H), 2.68–2.3 (m, 8H), 2.66 (s, 6H, $CH_3$), 2.29 (s, 3H, $CH_3$), 1.6–1.5 (m, 1H), 1.43–1.3 (m, 1H), 1.06 (t, 6H, $CH_3$), 0.92 (t, 1H); MS (CI,$NH_3$) m/e 357 (M+1).

Part F: Condensation to give the mono-imide (XI).

The amine X (22.1 g, 55.4 mmol) was dissolved in 500 mL of THF prior to the addition of 3-nitro-naphthalic anhydride (12.0 g, 49.5 mmol), and the resulting solution was refluxed 17 h. After cooling, the solution was concentrated under reduced pressure to an oil. Flash chromatography on silica gel provided 19.3 g (66%) of the imide XI as a foam. $^1$H-NMR (300 MHz, $CDCl_3$) $\delta$ 9.24 (d, 1H, aromatic), 9.06 (d, 1H, aromatic), 8.73 (d, 1H, aromatic), 8.38 (d, 1H, aromatic), 7.91 (t, 1H, aromatic), 6.88 (s, 2H, aromatic), 5.4 (m, 1H, CH), 3.59 (m, 1H, CH), 3.12 (m, 1H, CH), 3.01 (m, 1H, CH), 2.82 (m, 1H, CH), 2.70 (m, 1H, CH), 2.56–2.45 (m, 4H, $CH_2$), 2.52 (s, 6H, $CH_3$), 2.27 (d, 3H, $CH_3$), 1.58 (d, 3H, $CH_3$), 0.92 (d, 3H, $CH_3$); MS (CI,$NH_3$) m/e 582 (M+1).

Part G: Deprotection of the mesitylenesulfonyl group to give the amine XIII.

The imide XI (13.2 g, 22.7 mmol) was dissolved in 250 mL of 30% HBr/acetic acid prior to the addition of phenol (10.7 g, 113.5 mmol). This solution was heated at reflux for 4 h and then stirred at room temperature for 12 h. The solution was cooled to 0° C. and 300 mL of ether was added. The resulting solid was filtered and washed with ether to provide 12.3 g (84%) of the tri-hydrogen bromide salt XIII as a solid. m.p. 253°–254° C.; $^1$H-NMR ($D_2O$) $\delta$8.90 (d, 1H, 1 aromatic), 8.78 (d, 1H, aromatic), 8.50 (d, 1H, aromatic), 8.28 (d, 1H, aromatic), 7.76 (t, 1H, aromatic), 5.46 (m, 1H, CH), 3.90 (m, 1H), 3.64 (m, 1H), 3.5–3.18 (m, 7H), 1.56 (d, 3H, $CH_3$) and 1.27 (d, 3H, $CH_3$); MS (CI,$NH_3$) m/e 400 (free base) (M+1).

Part H: Condensation to give the bis-naphthalimide (I).

The tri-hydrogen bromide salt XIII (74.1 mg, 0.1 mmol) was dissolved in 5 mL of saturated $Na_2CO_3$ and extracted with methylene chloride. The methylene chloride was dried with $Na_2CO_3$, filtered, and concentrated in vacuo to give the free base. This free base was dissolved in 2 mL of THF prior to the addition of 1,8-naphthalic anhydride (19.8 mg, 0.1 mmol), and the resulting solution was refluxed 15 h. After cooling, the solution was concentrated to a crude oil. Flash chromatography on silica gel provided 40.3 mg (62%) of the freebase Ib. The freebase can be converted to the title compound (Ia) as described above in reference to Scheme A.

UTILITY

In Vitro Growth Inhibitory Activity

L1210 cells were maintained in RPMI-1640 a medium supplemented with 10% heat inactivated fetal bovine serum and 50 mL mercaptoethanol/liter medium (RPMI-L). B16 cells were maintained in RPMI-1640 medium supplemented with 15% heat inactivated fetal bovine serum and antibiotics (RPMI-C).

Exponentially growing murine leukemia L1210 cells ($1\times10^3$ cells) in 0.1 mL medium were seeded on day 0 in a 96-well microtiter plate. On day 1, 0.1 $\mu$L aliquot of medium containing graded concentrations of test analogs was added to the initial volume. After incubation at 37° C. in a humidified incubator for 3 days, the plates were centrifuged briefly and 100 mL of the growth medium was removed.

Exponentially growing human colon Clone A cells ($8\times10^2$) in 0.1 mL medium were seeded on day 0 in a 96-well microtiter plate. On day 1, 0.1 mL of medium containing graded concentrations of test analogs was added to the initial volume. After incubation at 37° C. in a humidified incubator for 6 days, the plates were centrifuged briefly and 0.1 mL of the growth medium was removed.

The cell cultures (above) were then incubated with 50 µL of 3-(4,5-dimethylthiazol-2-yl)-2,5-diphenyltetrazolium bromide (MTT; 1 mg/ml in Dulbecco's phosphate buffer saline) for 4 hours at 37° C. The resulting purple formazan precipitate was solubilized with 200 µL of 0.04N HCl in isopropyl alcohol. Absorbance was read in a Titertek Multiskan MCC scaning well spectrophotometer (Flow Laboratories) at a test wavelength of 570 nm and a reference wavelength of 630 nm.

The $ID_{50}$ values were determined by a computer program that fit all of the data (8 determinations per concentration and 12 concentrations per test analog) to the following equation:

$$Y=((Am-Ao)/(1+(X/ID_{50})n))+Ao$$

where: Am=absorbance of the control cells; Ao=absorbance of the cells in the presence of highest drug concentration; Y=observed absorbance; X=drug concentration; $ID_{50}$=dose of drug that inhibits the growth of cells to one half that of the control cells.

Results of the in vitro L1210 leukemia and Clone A colon carcinoma growth inhibition testing show that a representative compound of the invention, the compound of Example 1, has an $ID_{50}$ of 0.1 µg/mL and 0.0036 µg/mL, respectively.

In Vivo Tumor Models

Example 1, a representative compound of the present invention, has been tested in pre-clinical tests of anticancer activity which are indicative of clinical utility. The potent (<0.1 µg/mL) growth inhibitory activity against L1210 leukemia and Clone A colon carcinoma cell lines suggest that the compounds of the invention have the potential to be active in in vivo models. This was confirmed, since the presently claimed compound showed striking in vivo efficacy against human tumors xenografted in nude mice.

The methods used in the testing of compounds in the in vivo human tumor xenograft models are described below.

In Vivo Human Tumor Xenograft Models

The MX-1 human mammary carcinoma and the DLD-2 human colon carcinoma were originally obtained from a surgically removed primary breast tumor and colon carcinoma, respectively. The human tumor lines were maintained by serial passage in athymic nude mice. The MX-1 human mammary carcinoma is an established tumor used by the NCI. The MX-1 and DLD-2 tumor models have been well characterized.

The mice used in these experiments were outbred Swiss mice or BALB/c mice bearing the nude (nu/nu) gene. On day 0 male and female mice weighing 22–30 g are inoculated with 0.2 mL of a 25% tumor mince. This mince is prepared by mincing fresh tumor tissue, grown subcutaneously in passage mice, in sterile physiological saline. Palpable tumors weighing approximately 50 mg appear in the mice within 7–10 days after inoculation. The mice are pair matched by tumor weight and sex into groups of ten each and the test compounds and vehicle control are administered intravenously (i.v.) once daily for nine consecutive days. A >20% decrease in body weight on day 5 following compound administration is considered an indication of toxicity. Tumor measurements and body weights are recorded once a week. Fifteen to 18 days after the initial injection the mice are weighed, sacrificed and the tumors excised and weighed.

The efficacy of the test compounds is determined by the extent of tumor growth inhibition in treated versus vehicle-treated control mice. Initial tumor weights (mg) are calculated from the tumor dimensions (mm) measured from caliper measurements, using the formula for a prolate ellipsoid (mg of tumor weight=(length-×width$^2$)/2). Net tumor weights are calculated for each of the treated groups and the vehicle-treated control group by subtracting the initial tumor weight from the final tumor weight on day 15. Results are expressed as a percentage decrease relative to the mean tumor weight for the control vehicle-treated group.

% Tumor Growth Inhibition =

$$\left[ 1 - \frac{\text{mean tumor weight of treated}}{\text{mean tumor weight of control}} \right] \times 100$$

Activity Criteria

The criteria of the National Cancer Institute (NCI) for activity in the in vivo cancer models were used. Actual tumor regressions (IR=incomplete regression; FR=full regression) indicate excellent to outstanding activity. Tumor growth inhibition of ≧90% in the DLD-2 assay is condidered good to excellent and inhibition of 58–89% is considered moderate. Compounds demonstrating <58% growth inhibition are considered inactive.

The compound of Example 1 exhibited excellent to outstanding activity in the MX-1 human breast tumor model. In addition, the compound of Example 1 exhibited excellent to outstanding activity in the DLD-2 human colon tumor model. All of the compounds of the invention are expected to exhibit similar activity.

The demonstrated effectiveness of the compounds of the present invention in the human breast and colon tumor xenograft models indicate that the compounds of the present invention may be useful for the treatment of solid tumors in man, and, in particular, tumors of the breast and colon. This conclusion is further supported by published analyses correlating pre-clinical test results with clinical efficacy of anti-cancer agents. For example, see: Goldin and Venditti (1980) Recent Results Cancer Research 76: 176–191; Goldin et al. (1981) Eur. J. Cancer 17: 129–142; Mattern et al. (1988) Cancer and Metastasis Review 7: 263–284; Jackson et al. (1990) Cancer Investigations 8: 39–47. Based on these published analyses, the exceptional high level of antitumor activity exhibited by the presently claimed compounds provide strong evidence that the compounds claimed in present invention may have important therapeutic utility in the treatment of cancer in man.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 1 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addtion, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows.

Capsules:

Capsules are prepared by filling standard two-piece hard gelatin capsules each with 100 milligrams of powdered active ingredient, 175 milligrams of lactose, 24 milligrams of talc, and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstrach and 98 milligrams of lactose. Appropriate coatings may be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A compound having the formula (i):

(i)

[Chemical structure diagram showing a compound with substituents $R^{11}$, $R^{12}$, $R^3$, $R^4$, $R^5$, $R^6$, and an $O_2N$ group]

or enantiomeric or diastereomeric forms thereof, or mixtures of enantiomeric or diastereomeric forms thereof, and pharmaceutically acceptable salts thereof, wherein:

1) $R^{11}$ and $R^6$ are $CH_3$; and $R^{12}$, $R^3$, $R^4$, and $R^5$ are H; or 2) $R^{12}$ and $R^5$ are $CH_3$; and $R^{11}$, $R^3$, $R^4$, and $R^6$ are H.

2. A compound of claim 1 wherein:

$R^{11}$ and $R^6$ are $CH_3$; and $R^{12}$, $R^3$, $R^4$, and $R^5$ are H.

3. A compound of claim 2 selected from the following compounds, and pharmaceutically acceptable salts thereof:

(R,R)-2-{2-[2-((2-(1,3-Dioxo-1H-benz[de]-isoquinolin-2-(3H)-yl)-propylamino)) ethylamino]-1-methylethyl}-5-nitro-1H-benz[de]isoquinolin-1,3-(2H)-dione;

(S,S)-2-{2-[2-((2-(1,3-Dioxo-1H-benz[de]-isoquinolin-2-(3H)-yl)-propylamino)) ethylamino]-1-methylethyl}-5-nitro-1H-benz[de]isoquinolin-1,3-(2H)-dione;

(racemate+meso)-2-{2-[2-((2-(1,3-Dioxo-1H-benz-[de]-isoquinolin-2-(3H)-yl)-propylamino))e- thylamino]-1-methylethyl}-5-nitro-1H-benz-[de]isoquinolin-1,3-(2H)-dione; and (meso)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione.

4. A compound of claim 2 selected from the group consisting of:

(R,R)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione bis-methanesulfonate;

(S,S)-2-{2-[2-((2-(1,3-Dioxo-1H-benz[de]-isoquinolin-2-(3H)-yl)-propylamino))ethylamino]-1-methylethyl}-5-nitro-1H-benz[de]isoquinolin-1,3-(2H)-dione bis-methanesulfonate;

(racemate+meso)-2-{2-[2-((2-(1,3-Dioxo-1H-benz-[de]-isoquinolin-2-(3H)-yl)-propylamino))ethylamino]-1-methylethyl}-5-nitro-1H-benz-[de]isoquinolin-1,3-(2H)-dione bis-methanesulfonate; and (meso)-2-{2-[2-((2-(1,3-Dioxo-1H-benz[de]-isoquinolin-2-(3H)-yl)-propylamino))ethylamino]-1-methylethyl} -5-nitro-1H-benz[de]isoquinolin-1,3-(2H)-dione bis-methanesulfonate.

5. A pharmaceutical composition comprising a therapeutically effective amount of a compound of claim 1 and a pharmaceutical carrier.

6. A pharmaceutical composition comprising a therapeutically effective amount of a compound of claim 2 and a pharmaceutical carrier.

7. A pharmaceutical composition comprising a therapeutically effective amount of a compound of claim 3 and a pharmaceutical carrier.

8. A pharmaceutical composition comprising a therapeutically effective amount of a compound of claim 4 and a pharmaceutical carrier.

* * * * *